United States Patent [19]
Imahori et al.

[11] Patent Number: 4,584,272
[45] Date of Patent: Apr. 22, 1986

[54] ADENYLATE KINASE AND PROCESS FOR THE PRODUCTION THEREOF

[75] Inventors: Kazutomo Imahori, No. 2-25-23, Kakinokisaka, Meguro-ku, Tokyo; Hiroshi Nakajima; Kazuhiko Nagata, both of Kyoto, all of Japan

[73] Assignees: Unitika Ltd.; Rikagaku Kenkyusho; Kazutomo Imahori, all of Japan

[21] Appl. No.: 309,346

[22] Filed: Oct. 7, 1981

[30] Foreign Application Priority Data

Oct. 9, 1980 [JP] Japan .............................. 55-141405
Oct. 9, 1980 [JP] Japan .............................. 55-141406

[51] Int. Cl.$^4$ .................... C12N 9/12; C12P 19/32; C12R 1/07
[52] U.S. Cl. .................................... 435/194; 435/832; 435/92
[58] Field of Search ................................ 435/194, 92

[56] References Cited
FOREIGN PATENT DOCUMENTS
25088 2/1977 Japan .................................... 435/92

OTHER PUBLICATIONS

Konstantinova, Computer abstract of English Translation from Doklady Akademii Nauk SSSR Ser Biokhim, vol. 203 (1–6), No. 5 pp. 1204–1206 (pp. 121–122 of translation) 1972.
Lauwers et al, Chemical Abstracts 96: 2766k, 1982, abstract of Arch. Microbiol 1981, 130(2), 159–164.
Methods in Enzymology vol. 44, pp. 887–897.

*Primary Examiner*—Lionel M. Shapiro
*Attorney, Agent, or Firm*—Sughrue, Mion, Zinn, Macpeak and Seas

[57] ABSTRACT

A heat-resistant adenylate kinase is described whose activity after an incubation in a buffer solution at about 50° C. for about 15 minutes is at least about 80% of the original activity prior to the incubation. This adenylate kinase can be obtained by cultivating a bacterium belonging to the genus Bacillus and collecting adenylate kinase from the resulting culture broth. This heat-resistant enzyme is very stable against heat and, therefore, after isolation, it can be stored for a long period of time compared with the conventional adenylate kinase.

5 Claims, 2 Drawing Figures

ADENYLATE KINASE AND PROCESS FOR THE PRODUCTION THEREOF

FIELD OF THE INVENTION

The present invention relates to heat-resistant adenylate kinase and a process for the production thereof.

BACKGROUND OF THE INVENTION

Recently, enzymes have been widely used as industrial catalysts in view of the substrate specificity, reaction specificity, and stereochemical specificity thereof and mild reaction conditions. Such enzymatic catalysts, however, are limited to hydrolases which do not require an energy source, such as amylase hydrolyzing starch into saccharides, and L-amino acid acylase converting N-acyl-L-amino acid into L-amino acid.

Biosyntheses in vivo are carried out by synthetase utilizing mainly adenosine 5'-triphosphate (ATP) as an energy source, i.e., a chemical energy which is liberated when ATP is hydrolyzed into adenosine 5'-diphosphate (ADP) and orthophosphoric acid, or adenosine 5'-monophosphate (AMP) and pyrophosphoric acid. In order to extend industrial utilization of enzymes, therefore, it has been attempted to develop a new production system, generally called a "bioreactor", in which the same biosyntheses as in vivo are performed in vitro by fixing such synthetase or oxidoreductase and supplying ATP and the like. In the bioreactor system, a large amount of ATP is required as an energy source, and it is furthermore necessary to reproduce the ATP from the ADP or AMP.

For the reproduction of ATP from ADP or AMP, a method utilizing an enzyme, viz., adenylate kinase, catalyzing the following reaction is known, as described, for example, in *Enzyme Engineering*, Vol. 2, pp. 209 and 217 (1974).

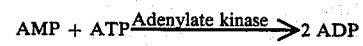  (1)

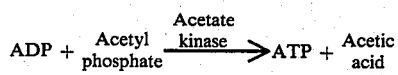  (2)

From (1)+(2)×2, the following equation becomes possible.

  (3)

That is, even though ATP is converted into ADP or AMP in the bioreactor system, the reproduction of ATP becomes possible by the combination (eq. (2) or (3)) of these enzymes.

In the practical utilization of such reactions, it is required for these enzymes to be stable and sufficiently durable for industrial applications. The heretofore known adenylate kinase, however, is a very unstable enzyme which is obtained from yeast and from muscles of animals. The acetate kinase, which is obtainable from *Escherichia coli*, is also very unstable, which has long been known.

More recently, however, Japanese Patent Application (OPI) No. 25088/77 (the term "OPI" as used herein refers to a "published unexamined Japanese patent application") disclosed that heat-resistant acetate kinase can be collected from a thermophilic *Bacillus stearothermophilus*. Thus, it has been desired to obtain adenylate kinase having high stability such as that for the acetate kinase described in Japanese Patent Application (OPI) No. 25088/77.

In commercially synthesizing compounds by the use of these enzymes, it is very difficult in practice to recover the enzyme after the reaction for the reuse thereof and to effect a continuous enzymatic reaction. In order to overcome such disadvantages, various investigations have been made, and several proposals have been made. One such proposal is to fix an enzyme on a water-insoluble carrier by a suitable method, to make the enzyme water-insoluble so that it can be used repeatedly. For instance, *Immobilized Enzyme* by Oskar Zaborsky, CRC Press (1973) and *Koteika Koso (Immobilized Enzyme)* by Ichiro Chibata, Kodansha (1975) give examples of immobilizing aminoacylase with ion exchange resin by adsorption, immobilizing dextranase with cellulose by covalent bonding, and immobilizing aspartase with polyacrylamide gel by entrapping. Such immobilization of enzymes is a typical method of permitting enzymes to be used repeatedly and continuously.

For example, it has been proposed to effect immobilization for the commercial development of acetate kinase (see *Hakko to Kygyo (Fermentation and Industry)*, Vol. 35, No. 1, pp. 3–10 (1977)). It has, however, been found that when a coliform enzyme is immobilized with cyanogen bromide according to Whitesides, et al., *Enzyme Engineering*, Vol. 2, p. 217 (1974), edited by E. Kendall et al., Prenum Press, the residual ratio of activity (expressed as a %) is only several % in the absence of a stabilizer, the long term stability is very poor, and the immobilized enzyme is not suitable at all for the commercial utilization thereof.

The factors inhibiting commercial utilization of enzymes includes the fact that almost all enzymes are very unstable, as well as the problem of water-solubility. Although examples in which immobilization increases the stability of the catalytic function are known, examples are also known in which the stability of the catalytic function is reduced. For example, I. Chibata concluded that, as a result of comparative examinations of the stability of enzyme before and after immobilization, that there could not be found any regularity between a method of immobilization and the stability of the immobilized enzyme, and therefore that it is very difficult to predict which method can increase the stability of enzyme (see I. Chibata, *Koteika Koso (Immobilized Enzyme)*, p. 107, Kodansha, Tokyo (1975). It is also known that in some cases, the properties which an enzyme has originally before the immobilization are lost by the immobilization, and the specificity is changed by the immobilization (see *Hakko to Kogyo (Fermentation and Industry)*, Vol. 35, p. 7 (1977)).

The properties of an enzyme result from the complicated and higher-order structure thereof. The higher-order structure of the enzyme is naturally influenced by the immobilization. Therefore, in order to know if a stable immobilized enzyme can be obtained by the immobilization, it is necessary to determine this by trial and error with each enzyme.

The molecular structure of the enzyme varies depending on the type of a microorganism producing the enzyme, and, furthermore, this complicated molecular structure easily changes depending on the circumstances under which the enzymatic protein is placed. Therefore, it is difficult for one skilled in the art to predict the properties, such as specificity, catalytic activity, and long term stability, of the enzyme after immobilization from the properties of the enzyme before immobilization. Therefore, when immobilization is performed using an enzyme of a different species even though the enzyme falls within the same category, it has not been possible to apply the immobilization method and conditions of the enzyme of the different species. In order to obtain an immobilized enzyme having a high residual ratio of activity and long term stability, therefore, it has been necessary to conduct investigations by the method of trial and error for each enzyme. For these reasons, it has long been desired to develop a method which permits the determination of a suitable immobilization method and immobilization conditions without relying on a trial and error method.

In the case of adenylate kinase, it has also been found that when it is to be immobilized for the commercial utilization thereof, the immobilization method and immobilization conditions must also be determined by the method of trial and error. This has seriously inhibited the immobilization of adenylate kinase and commercial utilization thereof. In fact, little study on the immobilization of adenylate kinase has been made. As one of a limited number of methods which have heretofore been reported, there is known, for example, a method in which adenylate kinase of pig muscle is immobilized in a polyacrylamide gel containing therein an N-hydroxysuccinimido group (see *Methods in Enzymology*, Vol. 44, p. 887 (1976), edited by K. Mosbach, Academic Press). In accordance with this known method, a complicated and delicate procedure is required so as not to deteriorate the activity of the enzyme, i.e., in the course of immobilization, adenylate kinase is added to a non-oxidizing atmosphere for several seconds until the acrylamide is solidified. The immobilization of adenylate kinase and application thereof have been subjected to significant limitations. In addition, adenylate kinase of pig muscle which cannot be immobilized on a carrier at the immobilization procedure usually loses the activity thereof, to the extent that it is practically impossible to recover and reuse. In accordance with these conventional methods, therefore, the immobilization of adenylate kinase and the production of adenine cofactors utilizing the immobilized adenylate kinase have not been practically possible. Even if adenylate kinase is immobilized irrespective of such operational and economical disadvantages, when the immobilization is performed at room temperature (20° to 30° C.), the activity is substantially lost, and, therefore, the immobilization should be performed at low temperature, e.g., near 0° C. In this respect, the production of immobilized adenylate kinase composite has been unfeasible from the viewpoint of operationability and economics.

SUMMARY OF THE INVENTION

An object of the invention is to provide heat-resistant adenylate kinase which is stabilized against heat and holds its activity over a long period of time, and a process for the production of the same.

Another object of the invention is to overcome the above-described disadvantages encountered in the immobilization of adenylate kinase by the conventional method, and to provide an immobilization method having excellent, economic and operational properties, and a novel immobilized adenylate kinase that remains stable over a long period of time.

As a result of extensive investigations to achieve the above objects, it has been found that adenylate kinase having the above-described properties is present in a cell of a microorganism belonging to the genus Bacillus, and furthermore that the adenylate kinase is a novel enzyme which can be easily purified and has surprisingly high stability compared with adenylate kinase present in yeast and the like.

Furthermore, as a result of investigations on the immobilization of such heat-resistant adenylate kinase by the method of trial and error, it has surprisingly been found that regardless of the kind of immobilization method is applied, the immobilized adenylate kinase composite material always has a catalytic capability and holds it stably over a long period of time unlike the conventional adenylate kinase. As a result of further investigations, it has been found that in the case of adenylate kinase, if the immobilization is performed using an enzyme which stands a certain heat-resistant test, the immobilized adenylate kinase obtained maintains its stable activity over a long period of time.

The present invention, therefore, relates to (1) heat-resistant adenylate kinase whose activity after an incubation in a buffer solution maintained at about 50° C. for about 15 minutes is at least about 80% of the original activity prior to the incubation, (2) a process for the production of heat-resistant adenylate kinase which comprises cultivating a bacterium belonging to the genus Bacillus and collecting heat-resistant adenylate kinase whose activity after an incubation in a buffer solutin maintained at about 50° C. for about 15 minutes is at least about 80% of the original activity prior to the incubation, (3) a stable immobilized adenylate kinase composite material prepared by bonding, adsorbing or entrapping heat-resistant adenylate kinase onto a water-insoluble carrier, and (4) a process for the production of a stable immobilized adenylate kinase composite material which comprises covalently bonding heat-resistant adenylate kinase onto a water-insoluble carrier.

The adenylate kinase of the invention is very stable against heat and, therefore, can be stored after isolation of the enzyme for a long period of time compared with the conventional adenylate kinase.

The stable immobilized adenylate kinase composite material as prepared by the invention can maintain its activity stably over a long period of time and, therefore, it is possible to provide a process for the conversion of adenine cofactors.

Therefore, it is possible to perform the so-called bioreactor system that the biosyntheses in vivo are carried out in vitro on a commercial scale.

DETAILED DESCRIPTION OF THE INVENTION

Figure 1:
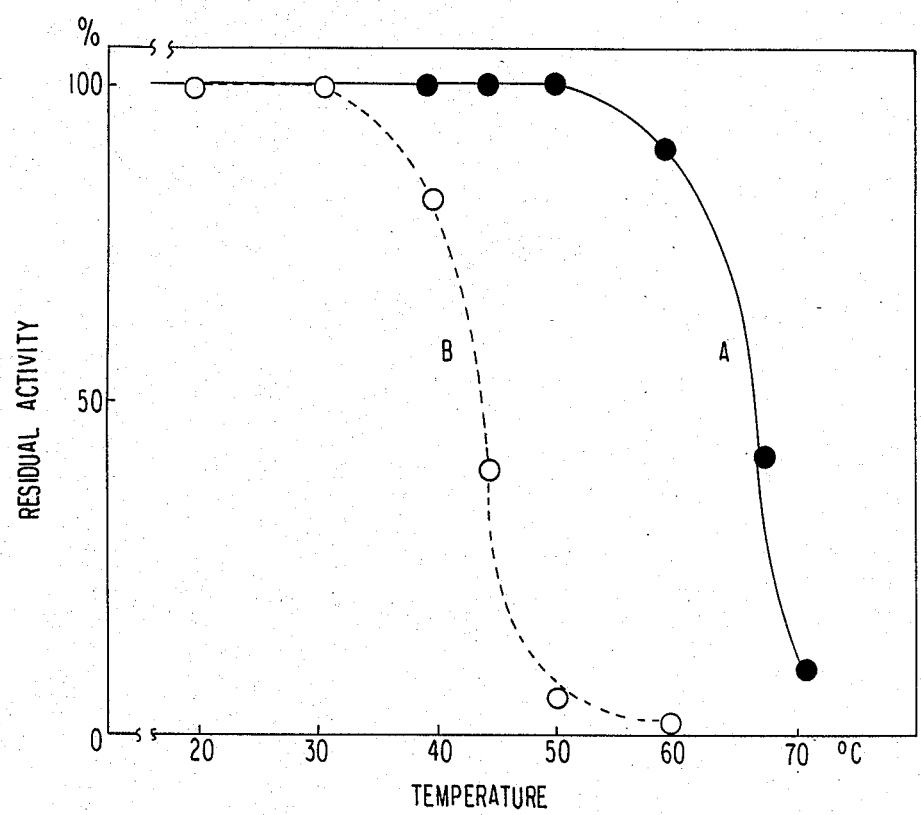
FIG. 1 is a graph showing the residual activity of adenylate kinase of the invention (Curve A) and adenylate kinase obtained from yeast (Curve B) after heating for 15 minutes at various temperatures.

The adenylate kinase of the invention, when treated in a buffer solution maintained at about 50° C. for about 15 minutes, retains a residual activity which is at least about 80%, preferably at least about 90%, and most preferably about 100%, of the original activity. In particular, the activity after a treatment in a buffer solution maintained at about 57° C. for about 15 minutes is at least about 80% of the original activity. Hereinafter, all of these properties are referred to as "heat-resistant properties".

The concentration and pH of the buffer solution are not critical. In general, however, the concentration is from 5 mM (millimolar) to 500 mM, and the pH is from 7 to 10.5. In particular, it is preferred in the invention to use a 50 mM phosphate buffer solution at a pH of about 7.5.

The preferred physical and chemical properties of the adenylate kinase of the invention are described below:

(1) Function of Enzyme

Catalyzes the following reaction:

AMP+ATP⇌2ADP

(2) Substrate Specificity

The Michaelis constants (km values) to AMP, ATP and ADP are 0.017 mM, 0.04 mM and 0.05 mM, respectively.

(3) Optimum pH

About 7.5 (temperature: 30° C.)

(4) Stable pH Range

Almost no inactivation occurs on application of a treatment within a pH range of 7.0 to 10.5 at 4° C. for 24 hours.

(5) Optimum Temperature Range

The activity increases with an increase in temperature from 25° C. to 65° C. at pH 7.5. Typically, the reaction is carried out at 30° C.

(6) Heat-Resistance

Retains an activity of 99% against heating at 57° C. for 15 minutes and remains stable.

(7) Molecular Weight

About 22,000, as determined by gel chromatography using Sephadex G-100.

(8) Determination of Activity

To an imidazole-hydrochloric acid buffer solution (75 mM; Ph of 7.2) are added 1.5 mM of AMP, 1.2 mM of ATP, 1 mM of magnesium sulfate, 135 mM of potassium chloride, 0.4 mM of phosphoenolpyruvic acid, 0.2 mM of reduction-type nicotineamide adenine dinucleotide (NADH), 5 unit(U)/ml of pyruvate kinase, and 10 unit-(U)/ml of lactate dehydrogenase to prepare a mixed solution. A suitable amount (0.1 to 0.002 unit per 1 ml of the mixed solution) of adenylate kinase is added to the mixed solution, whereupon the absorbance at 340 nm of NADH reduces with time. An enzymatic activity to reduce an absorbance at 340 nm in a ratio corresponding to 2 micromoles of NADH per minute is referred to as "one unit".

(9) Uniformity

A purified sample moves toward anode by acrylamide disc electrophoresis and provides a uniform band. Even by sodium dodecylsulfate(SDS)-gel electrophoresis, it provides a uniform band.

(10) Analysis

The amino acid content is shown below (mol%).

Aspartic acid 10.24%, threonine 3.65%, serine 1.87%, glutamic acid 12.05%, proline 6.06%, glycine 9.74%, alanine 7.64%, cystine (cystein) 0.80%, valine 7.37%, methionine 2.94%, isoleucine 10.55%, tyrosine 3.28%, phenylalanine 2.98%, lysine 5.86%, histidine 2.52%, arginine 7.17%, tryptophan 0.65%.

(11) Crystal Structure

Not determined, since it has not yet been crystallized.

The adenylate kinase of the invention can be prepared by cultivating a microorganism belonging to the genus Bacillus and collecting the adenylate kinase from the resulting cultivation product.

Any bacteria belonging to the genus Bacillus which are capable of producing the adenylate kinase of the invention can be used in the invention. A preferred example is *Bacillus stearothermophilus*. Typical examples of such stearothermophilus include ATCC Nos. 7953, 7954, 8005, 10149, 12980, NCA 1503, and UK-788 (FERM-P 5141).

Examples of carbon sources which can be used in the cultivation of such bacteria include saccharides such as glucose, sucrose, fructose, starch hydrolyzed products, molasses, and waste liquids of sulfite pulp; organic acids such as acetic acid and lactic acid; and alcohols, lipids, aliphatic acids, glycerine, and the like which are assimilable by the bacteria used. Example of nitrogen sources which can be used include organic and inorganic compounds such as ammonium sulfate, ammonium chloride, ammonium phosphate, ammonia, amino acid, peptone, meat extract, and yeast extract. In addition, as inorganic salts, salts of potassium, sodium, phosphoric acid, zinc, iron, magnesium, manganese, copper, calcium, cobalt and the like, and if necessary, small amounts of metal salts, corn steep, liquor, vitamins, nucleic acids, and the like may be used. Conventional nutrient medium can be used for practicing the process of the invention.

Using the thus-prepared culture medium, the bacterium belonging to the genus Bacillus is cultivated at from 20° C. to 80° C., preferably from 40° C. to 70° C., and most preferably at about 60° C., for from about 2 to 6 hours under aerated conditions. When the process of the invention is performed on a commercial scale, it is preferred to perform the cultivation continuously by adjusting a dilution ratio (hereinafter referred to simply as "D") as defined hereinafter to 0.9 or more of $\mu$ max of the bacterium used in the invention. That is, when the cultivation is performed continuously while maintaining D at 0.9 or more of $\mu$ max of the bacterium used in the invention, the adenylate kinase content of the cells produced exceeds the maximum value of adenylate kinase per unit cell obtained by a batchwise method. Furthermore, the productivity of cells is increased. In particular, when D is maintained near $\mu$ max, the adenylate kinase content of cells is increased to as much as about 1.3 times that obtained by a batchwise method. On the other hand, when the continuous cultivation is performed while maintaining D below 0.9 of $\mu$ max, the adenylate kinase content of cells is lower than that obtained by a batchwise method.

The dilution ratio, D, of the invention is expressed by the following equation:

$$D = \frac{F}{V} \qquad (1)$$

where
D: dilution ratio (1/hr)

F: rate at which a feed liquid is supplied to a fermentation tank, which is the same rate at which a cultivation product is withdrawn from the fermentation tank (l/hr)

V: amount of liquid in the fermentation tank (l)

The symbol "$\mu$ max" as used herein indicates the maximum specific growth rate (1/hr) of a bacterium under continuous cultivation conditions when the bacterium is continuously cultivated; that is, a specific propagation rate as determined when D is increased by a chemostat (see Herbert, Elsworth and Telling, *Journal of General Microbiology*, Vol. 14, No. 8, pp. 601–622 (1956)) and the cell concentration cannot be maintained at a constant level, i.e., the so-called wash-out phenomenon.

The determination of $\mu$ max using a thermophilic bacteria according to the invention is carried out as follows:

A 2 to 30 liter-fermentation tank is charged with 1.5 to 20 liters of a nutrient medium which is then inoculated with the bacterium while maintaining the temperature at from 40° to 75° C., and preferably 48° to 61° C., and a pH of 4.5 to 9.0, preferably 6.0 to 8.0. The bacterium thus-inoculated was batchwise cultivated. When the growth of the bacterium begins and the amount of the carbon source in the culture broth is reduced to 0.01% by weight or less, the continuous cultivation in which the common source alone is a growth-inhibiting factor is begun using a nutrient medium having the same composition as that charged to the fermentation tank. By so doing, the chemostat can be set up. After the continuous cultivation reaches a steady state, while D is stepwise increased, the cell concentration in the culture broth and the residual amount of the carbon source are with a lapse of time. D is further increased gradually. When D exceeds the specific propagation rate of the bacterium, the cell concentration holding a steady level begins to decrease, and contrarily, the carbon source concentration begins to increase. The rate at which the continuous cultivation cannot be maintained at a steady state if D is increased any more is called "wash-out". This specific propagation rate is referred to as "$\mu$ max".

Even though the same strain is used, the $\mu$ max greatly varies depending on the type of the nutrient medium used and cultivation conditions. However, if the combination is the same, the $\mu$ max exhibits a certain constant value. Therefore, if the $\mu$ max is determined once, it is reliable over a long period of time.

In the invention, the adjustment of D can be achieved by a method in which the cultivation is performed by the usual pre-cultivation and batchwise cultivation until the desired cell concentration is reached and, thereafter, the continuous cultivation is performed. The continuous cultivation can be begun at any time during the cultivation period. It is, however, advantageous that the continuous cultivation is begun at a later stage of the logarithmic propagation during the batchwise cultivation and is promptly fixed to the predetermined D.

An embodiment of the invention will hereinafter be described with reference to *Bacillus stearothermophilus* NCA 1503.

Using a nutrient medium with glucose as a carbon source, the chemostat was performed in a 30 liter-fermentation tank (20 liter charge) at the optimum temperature (57° C.) and pH (6.8) and $\mu$ max was measured and found to be 1.1 (1/hr). Thus, the continuous cultivation at D=$\mu$ max can be performed by a procedure in which a fresh nutrient medium having the same composition is continuously fed into a fermentation tank by the use of a pump in an amount of 1.1 times the charged amount per hour, i.e., at a rate of 22 l/hr according to the equation (1), while at the same time withdrawing the culture broth at the same rate.

The adenylate kinase of the invention is isolated from the culture broth. For example, the adenylate kinase can be isolated from any product such as a culture broth, isolated cells, processed products of isolated cells, crude enzyme, purified enzyme, and the like, which is produced in the culture and purification steps. For the purification, a conventional enzyme purification method can be employed (see Alan Wiseman et al., *Handbook of Enzyme Biotechnology*, Ellis Horwood Ltd. (1975)). For instance, cells can be collected by centrifugal separation or like procedure and pulverized by a Manton Gaulin, a Dyno-mill, a French press, a supersonic wave treatment, etc. Then, cell debris are removed by centrifugal separation to thus obtain a cell extract. The thus-obtained cell extract is subjected to streptomycin sulfate or protamin sulfate treatment in order to be precipitated nucleic acids. Furthermore, ammonium sulfate precipitation, acetone precipitation, heat treatment, and the like are applied. For the purification, ion exchange chromatography using a DEAE-cellulose column, etc., absorption chromatography using a hydroxyapatite column, etc., gel filtration chromatography such as Sephadex chromatography, and the like can be applied in combination with each other. In this way, the adenylate kinase of the invention can be isolated and purified.

Since the adenylate kinase of the invention is very stable against heat, it can be stored after the isolation for a long period of time compared with the conventional adenylate kinase.

The novel stable immobilized adenylate kinase composite material of the invention can be prepared by bonding or adsorbing the adenylate kinase as described above onto a water-insoluble carrier. For bonding the adenylate kinase onto the water-insoluble carrier, the heretofore known covalent bonding method or ion bonding method as described in, for example, I. Chibata, *Koteika Koso (Immobilized Enzyme)*, Kodansha, Tokyo (1975) can be employed. For the adsorption, a physical adsorption method and an entrapment method can be employed. In addition, a novel covalent bonding method using a 1-alkyl-2-halopyridium salt can be employed.

Examples of such covalent bonding methods include: a method in which a water-insoluble carrier containing, for example, a carboxyl group is treated with a 1-alkyl-2-halopyridium salt so that it is reactible with an amino group, a hydroxyl group, and a carboxyl group, and the adenylate kinase is then bonded thereto; a method in which a water-insoluble carrier containing an aromatic amino group is converted into a diazonium salt, and the adenylate kinase is diazo-coupled thereto; a method in which a carrier containing a carboxyl group is converted into a derivative such as azide, chloride, carbodiimide, or isocyanate, and the adenylate kinase is bonded thereto through a peptide bond; a method in which the adenylate kinase is bonded to a water-insoluble carrier containing an active releasing group, such as halogen; a method in which a water-insoluble carrier containing a hydroxyl group is treated with cyanogen halide, and the adenylate kinase is bonded to a water-insoluble carrier by the use of an at least two-functional reagent, e.g., a 1-alkyl-2-halopyridium salt, toluenediisocyanate, epichlorohydrin, glutaraldehyde, and 2-amino-4,6-dichloro-S-tolyazine.

As an ionic bonding method, use can be made of a method in which the adenylate kinase is ionically bonded to an ion exchange member, e.g., carboxymethyl cellulose, diethylaminoethyl Sephadex (produced by Pharmacia Corp.) and Dowex-50 (produced by Dow Chemical Corp.).

Also, as a physical adsorption method, use can be made, for example, of a method in which the adenylate kinase is adsorbed on active carbon, alumina, silica gel, or the like.

Also, as an entrapment method, use can be made, for example, of a method in which the adenylate kinase is entrapped in a lattice of polymeric gel, e.g., cross-linked polyacrylamide gel, and polyvinyl alcohol gel, or in a coating film of nylon, polystyrene, collodion, or the like.

This immobilization can be performed by a conventional procedure in which an aqueous solution of the heat-resistant adenylate kinase and a water-insoluble carrier or its precursor are mixed, if necessary, in the presence of a polymerization initiator. In the invention, however, it is not necessary to monitor the operation temperature so that the operation is performed at low temperatures, which is required for the conventional method. Thus, the immobilization according to the invention can be performed at ordinary temperatures (e.g., 20° C.–30° C.). This is one of major advantage of the invention.

As described hereinbefore, the stable immobilized adenylate kinase composite material of the invention can be prepared by various methods. Of these various methods, the covalent bonding method is particularly desired in that the bonding force between the adenylate kinase and the water-insoluble carrier is great, and therefore, the activity is very durable, for example, adenite cofactors can be converted stably over a long period of time. In particular, a covalent bonding method using an at least two-functional group-containing reagent, particularly a 1-alkyl-2-halopyridine salt, is preferred, in that mild immobilization conditions under which the inactivation of the adenylate kinase is rarely caused can be employed and the residual ratio of activity is high. In particular, a method is especially preferred in which a water-insoluble carrier previously containing a carboxyl group is reacted with a 1-alkyl-2-halopyridine salt in the presence of a deacidifier agent, and the heat-resistant adenylate kinase is covalently bonded thereto.

The production of the adenylate kinase composite material using the 1-alkyl-2-halopyridium salt can be carried out as follows:

A water-insoluble carrier containing a carboxyl group and from 1 to 1,000, preferably from 2 to 200, and most preferably from 2 to 20 mols, per mol of the carboxyl group of a deacidifier agent are mixed with a dehydrated organic solvent. Then, 1-alkyl-2-halopyridinium ions are reacted therewith in a ratio of from 1.2 to 1,200, preferably from 2.4 to 480 mols, and most preferably from 2.4 to 24 mols, per mol of the carboxyl group. The reaction can be carried out within the range of from ordinary temperature to the temperature at which the solvent boils. After the reaction is continued for more than 10 minutes, and preferably more than 1 hour, the reaction product is repeatedly washed with a dehydration solvent capable of dissolving the deacidifier agent. Thus, a water-insoluble carrier having an enzyme-bonding ability can be obtained.

The thus-obtained carrier is mixed with an aqueous solution of the heat-resistant adenylate kinase under the conditions of a temperature of from 0° to 50° C. preferably from 0° to 30° C., and most preferably from 0° to 20° C., and a pH of from 6 to 10, preferably from 7 to 9 and most preferably from 7 to 8, to thereby prepare an immobilized adenylate kinase composite material. The above mixing treatment is performed for a period of 2 minutes or more, preferably from 5 minutes to 10 hours, and most preferably from 10 minutes to 2 hours.

Alternatively, the adenylate kinase composite material using the 1-alkyl-2-halopyridium salt can be prepared by a method in which a water-insoluble carrier containing a carboxyl group, from 1.2 to 240, preferably from 2.4 to 120, and most preferably from 2.4 to 48 mols per mol of the carboxyl group, of 1-alkyl-2-halopyridium ions; from 2.4 to 480, preferably from 4.8 to 240, and most preferably from 4.8 to 98 mols per mol of the carboxyl group, of a deacidifier agent; and adenylate kinase are directly mixed with a water-organic solvent mixture. The amount of adenylate kinase used herein is from $10^6$ to $10^{10}$ units, preferably from $10^7$ to $10^9$ units, and most preferably from $10^7$ to $10^8$ units, per mol of the carboxyl group of the water-insoluble carrier. The pH of the water-organic solvent mixture is from 6 to 9, preferably from 6 to 8, and most preferably from 6.5 to 7.5. The temperature is generally 0° C. to 50° C., preferably from 0° C. to 30° C., and most preferably from 0° C. to 20° C. The treatment time is from 2 minutes to 5 hours, preferably from 2 minutes to 2 hours, and most preferably from 5 minutes to 2 hours. With regard to the ratio of water to organic solvent, the organic solvent is added in a proportion of from 0.6 to 6 parts by volume, and preferably from 0.8 to 1.2 parts by volume per part by volume of water.

In preparing the adenylate kinase composite material, various 1-alkyl-2-halopyridium salts can be used.

Examples of alkyl groups which can be used include straight alkyl groups such as methyl, ethyl, n-propyl, n-butyl and n-dodecyl, side chain-containing alkyl groups such as isopropyl, tert-butyl and neopentyl, cyclic alkyl groups such as cyclopentyl and cyclohexyl, and the foregoing alkyl groups containing aromatic rings, e.g., phenyl and naphthyl, and/or cyclic alkyl groups, e.g., cyclopentyl and cyclohexyl, and/or unsaturated alkyl groups, e.g., vinyl butynyl and isobutynyl. As the halogen at the 2-position of the 1-alkyl-2-halopyridium salt, there can be mentioned halogen atoms such as flourine, bromine, chlorine and iodine.

Examples of counter ions constituting the pyridium salt include halogen ions, such as fluorine, bromine, chlorine and iodine, organic anions, such as tosylate and prosylate, and coordinate type anions such as fluoro sulfate and tetrafluoro borate.

Examples of deacidifier agents which can be used include bases containing no active hydrogen, such as bases, e.g., triethylamine, trimethylamine, methyldiethylamine, pyridine and lutidine, and super bases, e.g., 1,8-diazabicyclo[5,4,0]-7-undecene and 1,5-diazabicyclo[4,3,0]-5-nonene.

Organic solvents which can be used include hydrocarbons such as benzene, toluene, xylene and cyclohexane, alcohols such as methyl alcohol, ethyl alcohol, amyl alcohol, cyclohexanol, ethylene glycol, glycerol, ethylene glycol monomethyl ether, and diethylene glycol, ethers such as diethyl ether, diamyl ether, benzyl ether, dioxane, tetrahydrofuran, and ethylene glycol dimethyl ether, ketones such as acetone, methyl ethyl ketone, and cyclohexane, esters such as ethyl acetate, propyl propionate, butyl formate, and butyl acetate, halogenated hydrocarbons such as chloroform, methylenechloride, carbon tetrachloride, and triethylenebromine, nitro compounds such as nitrobenzene, and nitromethane, nitriles such as acetonitrile and benzonitrile, and amides such as diethylformamide dimethylacetamide, and N-methylpyrrolidone.

The water-insoluble carrier as used herein indicates a compound which is substantially insoluble in water. Examples such as water-insoluble carriers include derivatives of polysaccharides such as cellulose, dextran, agarose and starch; cellulose polyacetate; certain derivatives of polyvinyl alcohol (e.g., water-insoluble derivatives cross-linked); polymers prepared from unsaturated carbon-containing monomers, such as polystyrene, polypropylene, polyethylene, polyvinyl chloride, polymethyl methacrylate, polybutene, polypentene, polyvinylidene chloride, polyacrylic acid, polyaminostyrene, polybutadiene, polyisoprene, poly(maleic acid monoester), cross-linked polyacrylamide, polyvinyl amine, poly(dialkylaminoethyl methacrylate), poly(dialkylaminomethylstyrene), poly(vinylpyridine), poly(-vinylpyrrolidone), poly(acrylic anhydride), poly(methacrylic anhydride), poly(maleic anhydride), polymethacrylonitrile, poly(trifluoroethylene), poly(tetrafluoroethylene), poly(divinylbenzene), poly(α-methylstyrene), poly(N-vinylamine), poly(tetramethylene glycol divinyl ether), polyvinyl sulfone, polyvinyl sulfoxide, polyacrolein, and poly(methylvinyl ketone); polyethers such as polyphenylene oxide, polymethylene oxide, polyethylene oxide, and polytetramethylene oxide; polypeptides such as polyalanine and polyphenylalanine; polyamides such as nylon-3, nylon-4, nylon-5, nylon-6, nylon-7, nylon-11, nylon-12, nylon-6,6, nylon-6,10, poly(m-phenylene-isophthalamide), and poly(p-phenyleneterephthalamide); polyesters prepared from polycarboxylic acids, e.g., terephthalic acid, isophthalic acid, adipic acid, maleic acid, fumaric acid, and trimellitic acid, and polyols, e.g., ethylene glycol, propylene glycol, butylene glycol, pentaerythritol, and bisphenol A; polyesters prepared from glyceric acid, lactic acid, and hydroxypivalic acid; silicone rubbers such as dimethyl polysiloxane, methylphenyl polysiloxane, methylvinyl polysiloxane, cyanoalkylmethyl polysiloxane, and fluoroalkylmethyl polysiloxane; polyurethanes prepared from polyisocyanates, e.g., toluene diisocyanate, phenylene diisocyanate, ethylene diisocyanate, diphenylmethane diisocyanate, and toluenetrisisocyanate, and polyols e.g., polyethylene glycol, polypropylene glycol, and polyesters containing OH groups at the terminals thereof; formaldehyde resins such as a phenol-formaldehyde resin, a xylene-formaldehyde resin, a urea-formaldehyde resin, and a melamine-formaldehyde resin; polyimides; 4-membered-ring-containing polymers such as polybenzimidazole and polythiazole; polycarbonates, polysulfones; inorganic derivatives, such as glass, asbestos, clay, mica, hydroxylapatite, active carbon, silica gel, and alumina; and synthetic inorganic polymers such as polyphosphergen.

Some of the major advantages of the process of the invention are listed below:

(1) The disadvantage that a suitable immobilization method should be determined for each adenylate kinase by the method of trial and error, which is required for the conventional methods, can be avoided.

(2) No complicated special procedures are required for the immobilization.

(3) Adenylate kinase which cannot be immobilized on a carrier can be recovered and used for the subsequent immobilization step.

The stable immobilized adenylate kinase composite material prepared by the invention can be used in various forms, for example, in the form of granules, fibers, a hollow-material, a film, a coated film, or the like, that is, as a stirring tank, a filling tank, a fluid tank, a tubular or film-type reactor, or the like for the conversion of adenine cofactors.

Since the stable immobilized adenylate kinase composite material prepared by the invention holds its activity stably for a long period of time, it is possible to provide a process for the conversion of adenine cofactors by the use of a reactor as described above. Thus, it becomes possible to perform the so-called bioreactor system that the same biosyntheses as in vivo are carried out in vitro on a commercial scale. The stable immobilized adenylate kinase composite material of the invention greatly contributes to the establishment of such a system on a commercial scale.

The following examples are provided to illustrate the invention in greater detail.

EXAMPLE 1 AND COMPARATIVE EXAMPLE 1

A culture medium comprising 0.5 g/dl (deciliter) of polypeptone, 0.5 g/dl of yeast extract, 1.0 g/dl of sucrose, 0.13 g/dl of potassium sulfate, 0.644 g/dl of disodium phosphate, 0.027 g/dl of magnesium sulfate, 0.032 g/dl of citric acid, 0.0007 g/dl of ferrous sulfate, and 0.015 g/dl of manganese sulfate was prepared and adjusted to pH 7.00. Then, 250 liters of the culture medium thus prepared was sterilized at 115° C. for 10 minutes and inoculated with *Bacillus stearothermophilus* NCA 1503 strain. The cultivation was conducted under aerobic conditions at 60° C. and a pressure of 0.5 kg/m$^2$G for 3 hours.

After the cultivation, cells were immediately collected with De Laval type centrifugal separator while cooling with water, and thus 700 g of cells were obtained. The thus-obtained cells were stored in a frozen state. Three hundred grams of the frozen cells were suspended in a 0.1M phosphate buffer solution (pH 7.5) whose volume was about 2 times the volume of the frozen cells, and were fully broken using a French press. After the removal of cell debris by centrifugal separation, a crude extract containing adenylate kinase was obtained.

A 1% protamine sulfate solution was added to the crude extract in an amount of 300 ml per 600 ml of the crude extract, and they were then fully mixed. After sufficient stirring, precipitates were removed by centrifugal separation and a protamine supernatant liquid was obtained. To the thus-obtained supernatant liquid was gradually added solid ammonium sulfate to 60% saturation (4° C.) Precipitates formed were collected by centrifugal separation, again dissolved in 20 ml of a 0.1M phosphate buffer solution (pH 7.5), and dialyzed and desalted by 4 liters of a 0.1M phosphate buffer solution (pH 7.5).

The above-prepared crude enzyme solution was passed through a DEAE-cellulose column which had been equilibrated with a 20 mM phosphate buffer solution (pH 7.5) containing 2 mM mercaptoethanol and 2 mM sodium ethylenediaminetetraacetate, and eluted therefrom with a buffer solution prepared by adding potassium chloride to the above buffer solution. Near a concentration of potassium chloride of 0.14M, the desired adenylate kinase was eluted. This fraction was collected, concentrated, desalted, passed through a hydroxyapatite column which had been equilibrated with a 10 mM phosphate buffer solution (pH 7.5), and eluted with a phosphate buffer solution having a linear gradient of from 10 mM to 250 mM. Near a concentration of 120 mM, the desired adenylate kinase was eluted. This active fraction was concentrated, desalted, and was subjected to Ultrogel ACA-34 chromatography using as an eluate a 50 mM Tris-hydrochloric acid buffer solution containing 0.1M potassium chloride. The thus-eluted active fraction was passed through a DEAE-Sephadex A-50 column which had been equilibrated with a 30 mM phosphate buffer solution (pH 7.7) containing 2 mM mercaptoethanol and 2 mM sodium ethylenediaminetetraacetate, and eluted with a solution prepared by adding potassium chloride to the above buffer solution. As a result, near a concentration of potassium chloride of 0.2M, purified adenylate kinase was eluted.

The thus-obtained adenylate kinase moved toward the anode using acrylamide disc electrophoresis, providing a single band. Furthermore, when subjected to Sephadex G-100 chromatography, it provided a single peak at a molecular weight of about 22,000.

The yield was about 6 mg, and showed an activity of about 500 units per milligram of the enzyme.

Thereafter, comparative examination of the thus-obtained adenylate kinase with the adenylate kinase obtained from yeast in respect of stability was made (Comparative Example 1).

Figure 2:
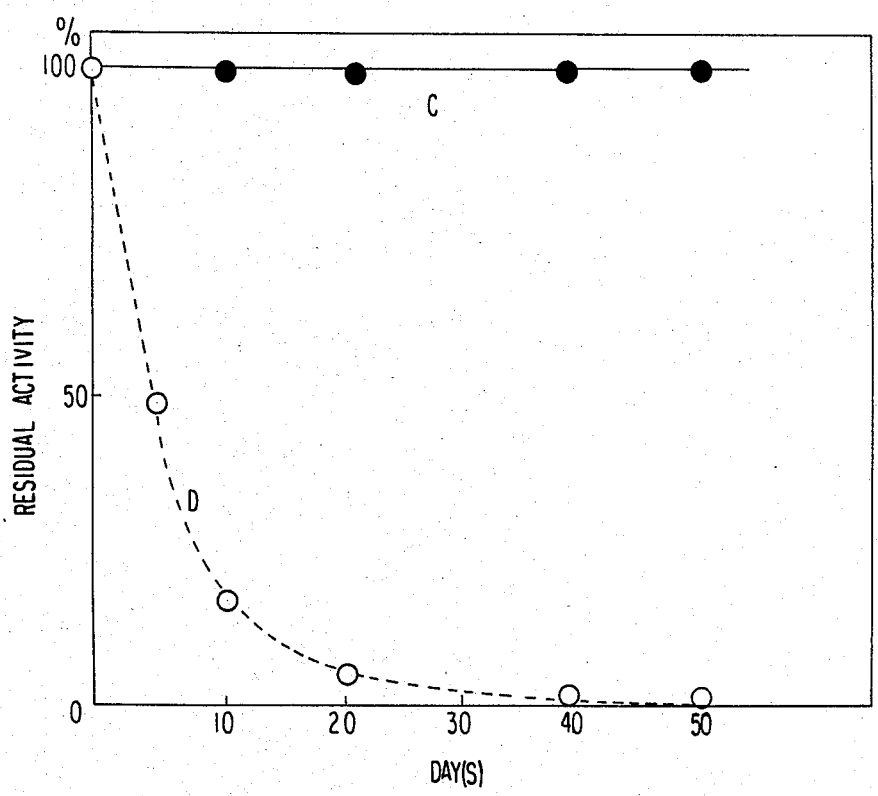
FIG. 2 is a graph showing the residual activity of adenylate kinase of the invention (Curve C) and adenylate kinase obtained from yeast (Curve D) after being allowed to stand at 30° C.

The results are shown in FIGS. 1 and 2. FIG. 1 is a graph showing the residual activity of the adenylate kinase when heated in a 50 mM phosphate buffer solution having a pH of 7.5 for 15 minutes at various temperatures. In FIG. 1, Curves A and B indicate Example 1 and Comparative Example 1, respectively. FIG. 2 is a graph showing a change with time of the reisdual activity of the adenylate kinase when stored in a 50 mM phosphate buffer solution having a pH of 7.5 at 30° C. In FIG. 2, Curves C and D indicate Example 1 and Comparative Example 1, respectively.

As is apparent from these results, the adenylate kinase obtained from yeast almost completely lost its activity irreversibly when it was incubated at 50° C. for 15 minutes, whereas the adenylate kinase of the invention did not lose the activity at all when it was incubated at 50° C. At a temperature of 30° C., the adenylate kinase obtained from yeast substantially lost the activity for 10 to 20 days, whereas with the adenylate kinase of the invention, no reduction in activity was observed at all even after 50 days.

Thus, it can be seen that the adenylate kinase of the invention is surprisingly stable against heat and can be stored for a long period of time. There are no conventional adenylate kinase having such properties.

EXAMPLES 2 TO 5

Strain Used

Bacillus stearothermophilus NCA 1503

Composition of Nutrient Medium

Prepared using glucose as a carbon source and by dissolving the following ingredients in 1,000 ml of running water: 1.3 g glucose, 1.0 g yeast extract (produced by Oriental Yeast Co., Ltd.), 0.5 g peptone (produced by Difico Co., Ltd.), 0.5 g $KH_2PO_4$, 0.5 g $Na_2HPO_4.12H_2O$, 0.1 g $MgSO_4.7H_2O$, 0.01 g, $ZnSO_4.7H_2O$, 0.01 g $MnSO_4.7H_2O$, 0.01 g $CuSO_4.5H_2O$, and 0.01 g $CoCl_2.6H_2O$.

First Cultivation

The nutrient medium having the above composition was divided into two portions. A 20 ml portion of the nutrient medium was placed in a 100 ml Erlenmeyer flask and the other 100 ml portion of the nutrient medium was placed in a 500 ml Erlenmeyer flask. After plugging the flasks with cotton, these nutrient media were steam-sterilized under pressure at 121° C. and 1 $kg/cm^2$ for 10 minutes. After being cooled, the 100 ml Erlenmeyer flask was sterilely inoculated with about 5 ml of a freeze dried cell obtained from American Type Culture Collection (ATCC). Using a rotary shaker (produced by Takasaki Seisakusho Co., Ltd.), rotary vibrational cultivation (160 rpm) was performed at 55° C. for one day and night. Growth of the cells was observed, and the turbidity increased. The absorbance at 660 nm (determined by the use of Model 101 Spectrophotometer produced by Hitachi Corp., hereinafter referred to as "OD 660 nm") reached from 0.8 to 1.0. Thus, the 500 ml Erlenmeyer flask was inoculated with about 5 ml of the seed culture in the 100 ml Erlenmeyer flask. With the thus inoculated 500 ml Erlenmeyer flask, rotary vibrational cultivation was performed under the same conditions as used in the case of the 100 ml Erlenmeyer flask for several hours. When OD 660 nm reached about 1.0, the rotary vibrational cultivation was stopped, and the culture broth thus-prepared was used as a seed culture for the following main cultivation.

Main Cultivation

Twenty liters of the above-prepared nutrient medium was placed in a 30 liter fermentation tank and sterilized at 121° C. and 1 $kg/cm^2$ for 15 minutes. The cultivation conditions were set to a temperature of 55±1° C., a pH of 6.5 to 7.0 (adjusted with 4N NaOH), an aeration amount of 20 liter/minute (air), with a stirring rate of 900 rpm. Then, the fermentation tank was inoculated with about 1 liter of the seed culture as prepared above, and batchwise cultivation was begun. As the cultivation proceeded, foams were formed and, therefore, a small amount of defoamer (KM-70 produced by Shin-etsu Chemical Co., Ltd.) was added thereto. In about 2.5 hours from the start of the cultivation, OD 660 nm reached 1.2 (0.56 g dry cell/liter), and almost all of the glucose in the culture medium was consumed and the glucose content was reduced to 0.01% by weight or less. Thus, promptly, the continuous cultivation was started. The $\mu$ max of the present strain which had been determined in advance was 1.4 (l/hr). Therefore, by supplying the foregoing sterilized nutrient medium continuously at a rate of 28.0 l/hr and withdrawing the culture broth from the fermentation tank at the same rate as above, the $\mu$ max was controlled to 1.00 (Example 2). Using five times as much of a nutrient medium as the liquid in the fermentation tank, continuous cultivation was carried out to obtain cells.

Then, D was stepwise changed to 0.9 (Example 3; rate of supply or withdrawal: 25.2 l/hr) and 0.75 (Example 4; rate of supply or withdrawal: 21.0 l/hr) of $\mu$ max, and continuous cultivation was performed to obtain cells.

With the thus-obtained cells, the adenylate kinase content was measured. The results are shown in Table 1. Table 1 also indicates the adenylate kinase content obtained by batchwise cultivation (Example 5), which is the adenylate kinase content of the cells obtained by the batchwise cultivation prior to the continuous cultivation.

TABLE 1

| Example | Adenylate Kinase Content (units/g dry cell) | Productivity of Cells (g dry cell/l/hr) | Productivity of Adenylate Kinase (units/l/hr) |
|---|---|---|---|
| 2 | 590 | 0.65 | 384 |
| 3 | 430 | 0.59 | 254 |
| 4 | 390 | 0.54 | 211 |
| 5 | 410 | 0.23 | 94 |

As apparent from Table 1, the adenylate kinase content of the cells produced under the condition that D is 0.9 or more of $\mu$ max is greater than that obtained by the batchwise method.

EXAMPLE 6

A culture medium prepared by dissolving 1.3 g of glucose, 1.0 g of ammonium sulfate, 0.5 g of yeast extract, 0.5 g of potassium phosphate, 0.5 g of dipotassium phosphate, and 0.1 g of magnesium sulfate in 1 liter of running water was charged to a 30-liter fermentation tank in the amount of 20 liters, and steam-sterilized at 121° C. and a pressure of 1 kg/cm² for 15 minutes. The cultivation conditions were set to a temperature of 57° C., a pH of 6.5 to 7.0 (adjusted by adding 4N NaOH), an aeration amount of 20 liter/minute (air), and a number of stirring. Thereafter, the culture medium was inoculated with 1 liter of a seed culture which has been prepared by pre-cultivating Bacillus stearothermophilus ATCC 12980 strain on the same culture medium as above and whose absorbance at 660 nm reached about 1.0. At the beginning, batchwise cultivation was performed for about 2.5 hours. When the absorbance at 660 nm reached 1.0, the sterilized nutrient medium having the same composition as above was continuously supplied to the fermentation tank at a rate of 24.0 liter/hr by the use of a quantitative pump, and the culture broth was withdrawn from the fermentation tank at the same rate as above. Thus, the continuous cultivation was performed using 100 liters of the nutrient medium to thereby obtain a culture broth. The thus-obtained culture broth was immediately separated by the use of a De Laval type centrifugal separator while cooling with water, to thereby obtain 400 g of cells.

The thus-obtained cell was suspended in 600 ml of a 0.1M phosphate buffer solution, and broken by the use of a Dyno-mill. After the removal of insoluble materials by centrifugal separation, a crude extract containing adenylate kinase was obtained. Then, 200 ml of a 10% streptomycin sulfate solution was added to 400 ml of the crude extract. Precipitates formed were removed by centrifugal separation to thereby obtain a streptomycin supernatant liquid. This supernatant liquid was subjected to ammonium sulfate fractionation, and a fraction from 30% saturation (4° C.) to 60% saturation (4° C.) was obtained. This fraction was dissolved in a 50 mM Tris-hydrochloric acid buffer solution (pH 8.0) and passed through a DEAE-Sephadex column which had been equilibrated with the same buffer solution as above, and thereafter it was eluted with a solution prepared by adding sodium chloride to the above buffer solution. Near a concentration of sodium chloride of 0.2M, the desired adenylate kinase was eluted. The thus-eluted fraction was subjected to hydroxyapatite column chromatography under the same conditions as in Example 1, passed through a Sephadex G-75 column, and eluted with a 30 mM Tris-hydrochloric acid buffer solution (pH 8.0) containing 0.1M sodium chloride to thereby obtain an adenylate kinase sample which provided a single band by acrylamide disc electrophoresis as in the case of Example 1. Furthermore, as in the case of Example 1, the adenylate kinase sample provided a single peak at a molecular weight of about 22,000 as determined by Sephadex G-100 chromatography.

The yield was about 10 mg, and the activity was about 500 units per milligram of the enzyme.

EXAMPLE 7 AND COMPARATIVE EXAMPLE 2

Five grams of CNBr activated Sepharose 4B (produced by Pharmacia Co.) was washed and swollen three times on a glass filter with 1,000 ml of 1 mM hydrochloric acid, and suspended in a 50 mM phosphate buffer solution (pH 8.3, 100 ml). The adenylate kinase obtained in Example 2 was dissolved in 1 ml of the above buffer solution (5,000 units) and reacted for 30 minutes while agitating slowing at 40° C. The reaction mixture was filtered with a glass filter. The thus-obtained immobilized adenyalte kinase composite material was washed three times with 200 ml portions of a 50 mM Tris-hydrochloric acid buffer solution (pH 8.0) containing 0.5M KCl. Filtrates obtained at all stages were collected, and the activity of the filtrate and immobilized adenylate kinase was measured.

Independently, using adenylate kinase obtained from pig muscle (produced by Boehringer Mannheim GmbH), the same test as above was repeated. The results are shown in Table 2.

TABLE 2

| | Source of Enzyme | Initial Activity (units) | Immobilized Activity (units) | Activity Recovered in Filtrate (units) |
|---|---|---|---|---|
| Example 7 | Bacillus stearothermophilus | 5,000 | 2,000 | 2,800 |
| Comparative Example 2 | Pig muscle | 5,000 | 50 | 200 |

The thus-prepared immobilized adenylate kinase composite material was suspended in a 500 mM phosphate buffer solution (pH 7.3) and allowed to stand at 30° C. The change in activity with a lapse of time was followed. The results are shown in Table 3.

It can be aseen from Table 3 that the composite material prepared from the adenylate kinase obtained from Bacillus stearothermophilus is surprisingly stable. The adenylate kinase recovered in the filtrate can be reused.

TABLE 3

| | Source of Enzyme | Just after Immobilization (units) | After 1 Month (units) | After 3 Months (units) | After 6 Months (units) |
|---|---|---|---|---|---|
| Example 7 | Bacillus stearothermophilus | 2,000 | 1,900 | 2,100 | 2,000 |
| Comparative | Pig muscle | 50 | 0.2 | 0.05 | — |

TABLE 3-continued

| Source of Enzyme | Just after Immobilization (units) | After 1 Month (units) | After 3 Months (units) | After 6 Months (units) |
|---|---|---|---|---|
| tive Example 2 | | | | |

EXAMPLE 8

Five hundred units of adenylate kinase obtained in Example 1 was washed and swollen (to three times initial volume) on a glass filter with 300 ml of 1 mM hydrochloric acid, and it was then added to 20 g of activated CH-Sepharose 4B (produced by Pharmacia Co.) which had been suspended in 50 ml of a 50 mM borate buffer solution. The resulting mixture was reacted for 1 hour while agitating slowing at 30° C. The reaction mixture was washed in the same manner as in Example 7. Then, the activity of the immobilized adenylate kinase composite material and the filtrate were measured and found to be 280 units and 210 units, respectively.

The immobilized adenylate kinase composite material was suspended in a 50 mM phosphate buffer solution (pH 7.3) and allowed to stand at 30° C. The change in activity with a lapse of time was monitored. The results are shown in Table 4. It can be seen from Table 4 that the immobilized adenylate kinase composite material shows excellent stability as in the case of Example 7.

TABLE 4

| Total Activity just after Immobilization (units) | After 1 Month (units) | After 3 Months (units) | After 6 Months (units) | After 12 Months (units) |
|---|---|---|---|---|
| 280 | 290 | 275 | 280 | 280 |

EXAMPLE 9

A 10% dichloromethane solution of tetrafluoroboric acid triethyloxonium salt maintained at a temperature of 30° C. was circulated through a nylon tube having an inner diameter of 0.2 mm at a flow rate of 0.1 ml/mm for 2 hours. The tube was then washed by circulating dichloromethane at a flow rate of 0.2 ml/mm for 5 minutes. Then, a 20% aqueous hexamethylenediamine solution was circulated through the tube of a flow rate of 0.1 ml/mm and a temperature of 30° C. for 1 hour. Then, the tube was washed with a 50 mM borate buffer solution (pH 8.3), and 5% (w/v) dimethyl suberimidate dissolved in the same buffer solution as above was circulated through the tube at a flow rate of 0.1 ml/mm and a temperature of 30° C. for 15 minutes. After washing the tube with methanol for 5 minutes, a 50 mM borate buffer solution (pH 8.3) containing 1,000 units of the adenylate kinase obtained in Example 2 was circulated through the tube at 30° C. After circulating for 2 hours, the tube was washed with the above buffer solution. The thus-recovered activity was 300 units, and the total activity immobilized onto the tube was 630 units.

With the immobilized adenylate kinase composite material, the change in activity with a lapse of time was followed in the same manner as in Example 7. The results are shown in Table 5. It can be seen from Table 5 that the adenylate kinase shows excellent stability.

TABLE 5

| Total Activity just after Immobilization (units) | After 1 Month (units) | After 3 Months (units) | After 6 Months (units) |
|---|---|---|---|
| 630 | 640 | 600 | 640 |

EXAMPLE 10

To 5 ml of a 20 mM phosphate buffer solution (pH 7.5) containing 0.29 g/ml of acrylamide, 6 mg/ml of N,N'-methylenebisacrylamide, and 0.1 mg/ml of riboflavin was added 10 units of a phosphate buffer solution (pH 7.5) of the adenylate kinase obtained in Example 6, and they were fully mixed at 0° C. Then, 50 μl of a 50 mg/ml potassium persulfate solution was added thereto. The resulting mixture was allowed to stand for 2 hours under a 20 W fluorescent lamp. The thus-obtained immobilized adenylate kinase-containing gel was pulverized with a grinder and then washed three times with 10 ml portions of a 20 mM phosphate buffer solution. As a result, the activity of the immobilized adenylate kinase was 8.3 units and the activity of the washing liquid was about 1.5 units.

The stability of the thus-prepared immobilized adenylate kinase composite material was measured in the same manner as in Example 8. The results are shown in Table 6. It can be seen from Table 6 that the immobilized adenylate kinase composite material shows excellent stability.

TABLE 6

| Just after Immobilization (units) | After 1 Month (units) | After 3 Months (units) | After 6 Months (units) |
|---|---|---|---|
| 8.3 | 8.5 | 8.0 | 8.3 |

EXAMPLE 11

Twenty grams of carboxymethyl cellulose (0.5 millimol of COOH) was washed three times with 1,000 ml of tetrahydrofuran which had been dehydrated with molecular sieves 4A, and it was then mixed with 1,000 ml of tetrahydrofuran. Then, 10 millimols of triethylamine and 12 millimols of 1-methyl-2-chloropyridium iodide were reacted therewith with stirring. The reaction mixture was then filtered. Crystals formed were washed with 1,000 ml of dehydrated chloroform ten times and with 1,000 ml of dehydrated tetrahydrofuran ten times. To the thus-prepared activated carboxymethyl cellulose was added 5,000 units of the adenylate kinase obtained in Example 2, which had been dissolved in a 50 mM borate buffer solution (pH 8.0), with stirring, and they were reacted at 30° C. for 1 hour. The reaction mixture was separated by filtration. The thus-obtained immobilized adenylate kinase composite material was washed with 1,000 ml of each of water and a borate buffer solution (pH 8.0). The composite material was soaked in 100 ml of a 500 mM ethanolamine-hydrochloric acid buffer solution (pH 8.0) for 4 hours and, thereafter, washed with 1,000 ml of a 50 mM phosphate buffer solution (pH 7.3) three times. The change with time of the immobilized activity and the activity as determined by the method as described in Example 7 were measured, and the results are shown in Table 7.

TABLE 7

| Just after Immobilization (units) | After 1 Month (units) | After 6 Months (units) | After 12 Months (units) |
|---|---|---|---|
| 3,000 | 3,000 | 2,950 | 3,100 |

EXAMPLE 12

Thirty thousand units of the adenylate kinase obtained in Example 1 and 10 grams of CH-Sepharose (produced by Pharmacia Co.) which had been washed and swollen with 500 ml of 1 mM hydrochloric acid and then with 1,000 ml of distilled water three times were suspended in a mixed solution of 250 ml of a 50 mM borate buffer solution and 250 ml of acetonitrile. Then, 2.4 millimols of tri-tert-butylamine and 1.2 millimols of 1-chloro-2-ethylpyridinium bromide were added thereto, and the resulting mixture was reacted at 20° C. for 30 minutes while agitating. The reaction mixture was passed through a glass filter. The thus-obtained immobilized adenylate kinase composite material was washed with 1,000 ml of a 500 mM ethanolamine-hydrochloric acid buffer solution and then with 500 ml portions of a 50 mM Tris-hydrochloric acid buffer solution containing 0.5M KCl (pH 8.0) five times. Finally, the composite material was washed with 500 ml portions of a 50 mM phosphate buffer solution three times. Filtrates at all stages were collected, and the activity of each of the filtrate and the immobilized adenylate kinase composite material was measured. The thus-prepared immobilized adenylate kinase was suspended in a 50 mM α-glycerophosphate buffer solution (pH 7.0) and allowed to stand at room temperature. After six months, the activity was measured. The results are shown in Table 8. It can be seen that the adenylate kinase composite material of the invention is surprisingly stable. The adenylate kinase recovered in the filtrate could be reused.

TABLE 8

| Initial Activity (units) | Immobilized Activity (units) | Activity Recovered in Filtrate (units) | Activity of Composite Material after 6 Months (units) |
|---|---|---|---|
| 30,000 | 18,000 | 10,000 | 17,500 |

EXAMPLE 13

Ten thousand units of the adenylate kinase obtained in Example 6 was dissolved in 500 ml of a 5 mM phosphate buffer solution (pH 7.1) while stirring for 1 hour, and 1 g of DEAE-Sephadex A-25 (produced by Pharmacia Co.) was added thereto. The resulting mixture was stirred at room temperature for 2 hours. The suspension thus-prepared was placed on a fritted glass filter and filtered. The thus-obtained insoluble material was washed five times with 500 ml portions of distilled water. Filtrates at all stages were collected, and the activity of each of the filtrate and the immobilized adenylate kinase composite material was measured. The thus-prepared immobilized adenylate kinase composite material was suspended in a 50 mM phosphate buffer solution (pH 7.1) and allowed to stand at room temperature. After 6 months and one year, the activity was measured. The results are shown in Table 9. It can be seen from Table 9 that the adenylate kinase composite material of the invention stably retains its activity even after one year.

TABLE 9

| Initial Activity (units) | Immobilized Activity (units) | Activity Recovered in Filtrate (units) | Activity of Composite Material after 6 Months (units) | Activity of Composite Material after One Year (units) |
|---|---|---|---|---|
| 10,000 | 7,000 | 2,800 | 6,500 | 6,300 |

Using the adenylate kinase (2,800 units) recovered in the filtrate, the procedure of this example was applied to 0.5 g of fresh DEAE-Sephadex A-25. As a result, an adenylate kinase composite material in which 2,000 units of activity was immobilized was obtained, and it could be reused in high efficiency.

While the invention has been described in detail and with reference to specific embodiments thereof, it will be apparent to one skilled in the art that various changes and modifications can be made therein without departing from the spirit and scope thereof.

What is claimed is:

1. A process for producing a heat-resistant adenylate kinase which comprises cultivating a bacterium belonging to the genus Bacillus having the ability to produce a heat-resistant adenylate kinase, and collecting therefrom heat-resistant adenylate kinase whose activity after an incubation in a buffer solution at about 50° C. for about 15 minutes is at least about 80% of the original activity prior to the incubation.

2. A process as in claim 1, wherein the cultivation is performed continuously under the conditions that the dilution rate (D) satisfies the mathematical relationship (a):

$$D \geq 0.9 \mu max \qquad (a)$$

wherein D indicates a dilution ratio, and $\mu$ max indicates the maximum specific growth ratio (1/hr) of the bacterium under continuous cultivation conditions.

3. A process as in claim 1 or 2, wherein the bacterium belonging to the genus Bacillus is *Bacillus stearothermophilus*.

4. A process as in claim 1 wherein after said collecting, said heat-resistant adenylate kinase is purified and/or immobilized on a water-insoluble carrier.

5. A process as in claim 4 wherein said heat-resistant adenylate kinase is bonded onto the water-insoluble carrier by a covalent bond.

* * * * *